United States Patent [19]

Cornils et al.

[11] Patent Number: 5,091,350

[45] Date of Patent: Feb. 25, 1992

[54] PROCESS FOR HYDROFORMYLATION WITH RHODIUM CATALYSTS AND THE SEPARATION OF RHODIUM THEREFROM

[75] Inventors: Boy Cornils, Dinslaken; Werner Konkol, Oberhausen; Helmut Bahrmann, Hamminkeln-Drunen; Hanswilhelm Bach; Ernest Wiebus, both of Oberhausen; Wolfgang Lipps, Isny, all of Fed. Rep. of Germany

[73] Assignee: Hoechst Aktiengesellschaft, Oberhausen, Fed. Rep. of Germany

[21] Appl. No.: 605,939

[22] Filed: Oct. 29, 1990

Related U.S. Application Data

[63] Continuation of Ser. No. 920,901, Oct. 16, 1986, abandoned, which is a continuation of Ser. No. 714,960, Mar. 22, 1985, abandoned.

[30] Foreign Application Priority Data

Mar. 26, 1984 [DE] Fed. Rep. of Germany ....... 3412335
Apr. 3, 1984 [DE] Fed. Rep. of Germany ....... 3411034

[51] Int. Cl.$^5$ .......................... B01J 23/96; B01J 38/68; C22B 11/04; C07C 45/50
[52] U.S. Cl. .......................................... 502/24; 423/22; 502/26; 502/27; 568/454
[58] Field of Search ....................... 502/22, 24, 26, 27; 423/22

[56] References Cited

U.S. PATENT DOCUMENTS 4,248,802 2/1981 Kuhtz ................................. 568/454
4,399,312 8/1983 Russell ............................... 502/162
4,731,485 3/1988 Cornils et al. ....................... 502/24

FOREIGN PATENT DOCUMENTS 0147824 4/1989 European Pat. Off. .
3347406 7/1985 Fed. Rep. of Germany .
2085874 5/1982 United Kingdom ............... 502/24

Primary Examiner—Paul E. Konopka
Attorney, Agent, or Firm—Bierman and Muserlian

[57] ABSTRACT

A process for separating rhodium from mixtures thereof, comprising extracting said rhodium with an aqueous solution of a rhodium complexing agent and a solubilizer. A process for preparing aldehydes in the presence of both the complexing agent and the solubilizer is also set forth. The solubilizer is generally selected from salts of carboxylic acids having 8-20 carbon atoms, alkyl sulfonates, alkyl aryl sulfonates, amines and quaternary ammonium compounds of Formula II

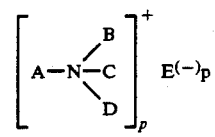

wherein A is alkyl, alkoxy, hydroxyalkyl, aryl having 6-25 carbon atoms, or $R^7CONHCH_2CH_2CH_2$— wherein $R^7$ is alkyl having 5-11 carbon atoms; B is an alkyl having 1-25 carbon atoms, an aryl having 6-25 carbon atoms, or an ω-hydroxy alkyl having 1-4 carbon atoms; C and D are each independently an alkyl or ω-hydroxy alkyl having 1-4 carbon atoms or form, together with each other and the bridging N, a 5 or 6 membered heterocyclic ring; E is a halide, sulfate, borate, sulfonate, lactate or citrate; and p is the number of charges on E. The rhodium complexing agent is preferably a triaryl phosphine carboxylate or sulfonate.

10 Claims, No Drawings

PROCESS FOR HYDROFORMYLATION WITH RHODIUM CATALYSTS AND THE SEPARATION OF RHODIUM THEREFROM

PRIOR APPLICATION

This application is a continuation of U.S. patent application Ser. No. 920,901 filed Oct. 16, 1986, which is a continuation of U.S. patent application Ser. No. 714,960 filed Mar. 22, 1985, both now abandoned.

The present invetion relates to improved methods of recapturing rhodium from various mixtures. It is especially related to the recovery of rhodium from hydroformylation reaction product mixtures.

The preparation of aldehydes and alcohols by the addition of carbon monoxide and hydrogen to an olefinic double bond, hydroformylation, is a well known process. It is catalyzed by metals in Group VIII of the Periodic Table or compounds thereof which are capable of forming carbonyls or hydridocarbonyls under the reaction conditions. Previously, cobalt and cobalt compounds were primarily used as hydroformylation catalysts, but rhodium catalysts are becoming increasingly important.

Rhodium is employed, in these reactions alone or as a complex. The complexes finding greater and greater applications are primarily complexes of rhodium with organic phosphines. The uncomplexed rhodium generally catalyzes the. Oxo synthesis (hydroformylation reaction) at pressures of 250-300 bar ($2.5 \times 10^4$ to $3 \times 10^4$ kPa). Complexed rhodium permits the reaction to take place at 10-50 bar ($1 \times 10^3$ to $5 \times 10^3$ kPa).

The rhodium catalysts are becoming increasingly valuable in hydroformylations because they demonstrate clear advantages over the analogous cobalt catalysts. The rhodium mediated reactions result in greater selectivity (n-aldehydes being preferred over iso aldehydes), greater activity, and fewer problems in operating the plant, especially in the operation of, and removal of the products from, the reactor. Also, there is a lesser tendency to produce saturated hydrocarbons with rhodium catalyzed reactions than when cobalt catalysts are used. A still further advantage of the rhodium catalyzed hydroformylation reaction is that existing equipment used for cobalt catalyzed reactions can be converted to rhodium catalyzed reactions with relatively little capital investment.

It has been found that rhodium catalysts, without complexing agents, persist in remaining in the hydroformylation reaction product. Full separation and recovery of the rhodium is extremely difficult.

In the work-up, the Oxo raw product is usually depressurized in several stages by reducing the synthesis pressure, which typically is about 250 to 300 bar ($25 \times 10^3$ to $30 \times 10^3$ kPa). This causes the release of the synthesis gas, which is dissolved in the raw product. Once the dissolved synthesis gas is given up, the pressure can be further reduce,d to normal atmospheric pressure. Generally, the depressurized raw product is then distilled to obtain the desired product.

However, there are several drawbacks to distillation. It must be remembered that the aldehydes and alcohols formed during the hydroformylation reaction are thermally sensitive. This is especially so regarding the organic products of larger molecular weight, i.e. over 5 carbon atoms, which require higher distillation temperatures. Furthermore, under those conditions, it has been found that the rhodium catalysts decompose resulting in substantial catalyst losses.

Furthermore, the precious metal is homogeneously dissolved in the raw product in a concentration of only a few ppm. Further difficulties can also arise owing to the fact that, during depressurization, the rhodium is converted to its metallic form or forms polynuclear carbonyls. Whatever form the catalyst metal takes when present during distillation, a heterogenous system is formed which consists of (a) the liquid organic phase and (b) the solid phase containing rhodium or rhodium compounds. Therefore, before purification or further processing of the reaction product (distillation), the dissolved rhodium compounds must be removed.

In German Application P 33 47 406.0, rhodium is separated and recovered from hydroformylation reaction products by extracting the raw product with a complexing agent. It should be understood that "raw product" is intended to mean that mixture resulting from the hydroformylation reaction after depressurization to about atmospheric pressure and any necessary cooling has occurred.

According to one preferred embodiment of the procedure, the complexing agents used are sulfonates and carboxylates of organic phosphines having the general formula:

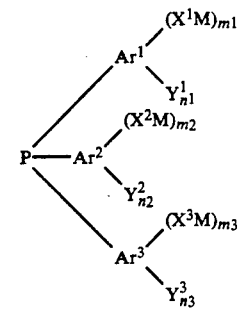

I wherein $Ar^1$, $Ar^2$ and $Ar^3$ each represent a phenyl or naphthyl group; $Y^1$, $Y^2$ and $Y^3$ are each independently a straight or branched alkyl having 1 to 4 carbon atoms, alkoxy, halogen, OH—, CN—, $NO_2$—, or where $R^1$ and $R^2$ each represent a straight or branched alkyl having 1 to 4 carbon atoms; $X^1$, $X^2$ and $X^3$ are each a carboxylate (COO——) and/or a sulfonate ($SO^-_3$—); $m_1$, $m_2$ and $m_3$ are the same or different whole numbers from 0 to 3, the sum of $m_2$, and $m_3$ being at least 1; and $n_1$, $n_2$, and $n_3$ are the same or different whole numbers from 0 to 5. M is an alkali metal ion, an equivalent of an alkaline earth metal ion or zinc ion, ammonium, or quaternary ammonium ion with the general formula $N(R^3R^4R^5R^6)^+$ wherein $R^3$, $R^4$, $R^5$, and $R^6$ are each independently selected from straight or branched alkyls having 1 to 4 carbon atoms. In one preferred embodiment, $Ar^1$, $Ar^2$, and $Ar^3$ are each a phenyl group; $X^1$, $X^2$, and $X^3$ are each a sulfonate group; and $m_1$, $m_2$, and $m_3$ are each independently 0 or 1, provided at least one of $m_1$, $m_2$ and $m_3$ is 1.

The complex compounds formed from rhodium and the sulfonates or carboxylates of organic phosphines are water-soluble. Thus the rhodium can be extracted from the Oxo raw product, i.e. the organic phase, with an aqueous solution of the substituted phosphine. The rhodium thereby passes into the aqueous phase, which can be separated from the organic product mixture by simple decanting. By cycling the solution of the complexing agent, high rhodium concentrations can be achieved in the aqueous phase.

DES 26 27 354 has described the use of water soluble rhodium complexes of triarylphosphines as catalysts. Essentially, this disclosure teaches that the complex formed in the extracting process of German Application P 33 47 406.0 can be recycled, as is, as a catalyst. In this version, the catalyst naturally migrates to the aqueous phase allowing separation of major amounts of the catalyst from the desired product by mere decantation or other separation methods not involving deleterious heating steps.

Even with the extracting complexing agent or the complexed catalyst, it has been found that the rhodium contained in the product mixture is still insufficiently recovered therefrom. Additionally, when higher olefins are used as starting materials, conversions drop appreciably thereby decreasing the economic viability and worth of the process on a commercial scale. This drop in activity is quite understandable, since the hydroformylation reaction takes place in the aqueous phase and the higher olefins are less and less soluble therein.

DE 31 35 127 A1 discloses conducting the hydroformylation reaction with aqueous and organic phases which are either immiscible or only slightly miscible with each other. Although solubilizers are mentioned, the reaction is limited to rhodium complexes with monosulfonated triaryl phosphine or monocarboxylated triarylphosphine. This limited application is a severe drawback as it is well known that monosulfonated triaryl phosphines have extremely short life spans, making them unsuitable for recycling without extensive workup.

One object of the present invention is to provide a process which allows for the nearly total recovery of the rhodium present in a mixture.

Another object is to provide a method of obtaining purified hydroformylation products easily and cheaply.

A third object is to develop a procedure for carrying out hydroformylation reactions with higher olefins in high yields.

A still further object is to recover rhodium catalyst in a state which allows for recycling without substantial workup thereof.

Surprisingly, these and other objects are achieved by the present invention. It is essentially a process for the recovery of rhodium from mixtures in general, with specific application to reaction product mixtures resulting from hydroformylation reactions one phase of the invention comprises extracting a mixture containing rhodium with an aqueous solution having both a rhodium complexing agent and a solubilizer. A second phase of the invention is conducting the hydroformylation reaction in the presence of the complexing agent and solubilizer.

The complexing agent is preferably a triaryl phosphine carboxylate or sulfonate, especially those having Formula I above. The complexing agent and solubilizer may be present in the hydroformylation reaction medium before the reaction begins or added during its progress. In addition to promoting the extraction of rhodium from the organic reaction products, the solubilizers, In the presence of the trisulfonated or tricarboxylated triaryl phosphine complexes of rhodium yield consistently high conversions and selectivities while avoiding catalyst decomposition. In this connection the phosphines are those of Formula I above but the sum of $m_1$, $m_2$ and $m_3$ must be at least 3.

The solubilizers of the invention are understood to be substances or mixtures of substances which are compatible with both the aqueous and the organic phase and, in particular, are soluble in both phases at elevated temperatures. Such substances are known and are also called phase transfer, surface-active or amphiphilic reagents or tensides.

Their particular effect is that they alter the physical properties of the contact surfaces between the two liquid phases and, thus, accelerate the transfer of the aqueous extracting agent to the product phase and the rhodium from the product phase to the aqueous complexing agent phase.

The use of the solubilizer simplifies extraction and reduces the amount of equipment necessary. With the new process it is possible to recover more than 95% of the rhodium contained in the product phase. Hence, one of the most important prerequisites for the technical realization of rhodium catalyzed hydroformylation, the separation of rhodium from the product is achieved. In this connection it is particularly advantageous that the solubilizer have no negative affect on the activity of the catalytically-active metal; hence, no special work-up or activation steps are required. However, variations requiring work-ups of differing degrees will be apparent to those in the art and are not excluded from the scope of the invention.

Examples of anionic solubilizers which can be used in the process according to the invention are salts of carboxylic acids having 8 to 20 carbon atoms, in particular of saturated fatty acids with 12 to 18 carbon atoms such as lauric, myristic and stearic acids. Alkyl sulfonates and alkyl aryl sulfonates, such as alkyl benzene sulfonates and alkyl naphthalene sulfonates are also anionic solubilizers within the scope of the invention.

Amines whose higher molecular group is bonded to the nitrogen atom, either directly or via a heteroatom, can be used as cationic solubilzers. Examples of the first group of the above-mentioned compounds are octadecyldiethylamine, octadecylethanolamine, lauryldipolyglycolamine and 2-heptadecylimidazoline hydrochloride. The second group contains, in particular, compounds with hydrolysis-stable ether groups such as octylphenoldiethylamine ethylglycol ether.

Quarternary ammonium compounds, especially ammonium salts, are particularly suitable cationic solubilizers. Compounds of Formula II

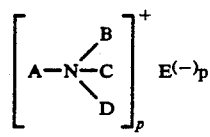

have been found to be particularly suitable. In this formula, A is selected from (a) straight or branched alkyl, alkoxy, hydroxyalkyl (especially ω-hydroxyalkyl), each having preferably 1-25 carbon atoms, (b) substituted or unsubstituted aryl having 6 to 25 carbon atoms, or (c) $R^7$—CONH—$CH_2$—$CH_2$—$CH_2$, where $R^7$ is a straight or branched alkyl having 5 to 11 carbon atoms; B is a straight or branched alkyl having 1 to 25 carbon atoms, substituted or unsubstituted aryl having 6 to 25 carbon atoms, or ω-hydroxyalkyl having 1–4 carbons atoms; C and D are the same or different and are selected from (a)

straight or branched alkyl groups preferably having 1-25 carbon atoms, or (b) ω-hydroxy alkyl having 1 to 4 carbon atoms, or C and D, together with the bridging N, form a five or six-membered heterocyclic ring; E denotes chloride, bromide, iodide, sulfate, tetrafluoroborate, acetate, methosulfate, benzene sulfate, alkyl benzene sulfate, toluene sulfonate, lactate or citrate, and p is the number of charges on E.

The methosulfates, sulfonates and lactates are preferred as anions because of their relatively low corrosive action. Examples of suitable cations include stearyltrimethylammonium, phenyltrimethylammonium, benzyltrimethylammonium, dimethylbenzyldodecylammonium, cetyltrimethylammonium, myristyltrimethylammonium, dodecylpyridinium, stearylamidomethylpyridinium, cetyldimethylbenzylammonium, distearyldimethylammonium, lauryltrimethylammonium, benzyltriethylammonium, N-(3-trimethylammoniumpropyl)-n-heptanoic acid amide methosulfate, N-(β-trimethyl-ammoniumpropyl)-n-nonanoic acid amide methosulfate and dodecyl-tris-β-hydroxyethylammonium.

The neutral or non-ionoic solubilizers are, in particular, adducts of ethylene oxide, such as alkylpolyethylene glycols (obtained by the addition of higher molecular alcohols to ethylene oxide), alkylphenylpolyethylene glycols (obtained by the addition of phenols to ethylene oxide and acylpolyethylene glycols (obtained by the addition of fatty acids to ethylene oxide). Polar solubilizers such as sulfolane and dimethyisulfoxide are also suitable.

It is advantageous if the solubilizer contains both polar and non-polar molecular components so that the required activity for both the aqueous and the organic phases is ensured. In particular, the solubilizer should be distributed that means solved preferably in the aqueous phase and only to a lesser extent in the organic phase. The solubilizers can be used alone or as mixtures.

The concentration of the solubilizer in the aqueous solution is about 0.005 to about 10% by weight based on the solution, preferably about 0.1 to about 2.5 % by weight and most preferably about at least 0.5% by weight. Concentrations above 2.5% by weight can increase foaming tendency, to a greater or lesser extent, depending on the selected solubilizer, thus impairing rapid phase separation.

The process according to the invention is used with particularly great success for the separation and recovery of rhodium from the products of hydroformylation of both terminal and non-terminal branched olefins with at least 4 carbon atoms. Even greater results are obtained with olefins having more than 5 carbon atoms such as 1-heptene, diisobutylene, tri- and tetrapropylene or the mixture of $C_8$-olefins sold under the trade name Dimersol. Naturally, the process can also be employed for the hydroformylation of unbranched terminal and non-terminal olefins; however the absolute rhodium concentrations in these reactions are generally lower to start with.

The uncomplexed rhodium catalyzed hydroformylation reaction is generally carried out at about 250 to about 300 bar and 120° C. to 150° C. The complexed rhodium catalyzed reaction may be conducted at about 1 to about 2 bar, preferably about 10 to about 100 bar, and more preferably at about 10 to about 50 bar. Suitable temperature ranges are generally about 20° C. to about 150° C., preferably about 50° C. to about 120° C.

The complexed catalyst can be added to the reaction mixture in a preformed state, or formed in situ. The complex may even be formed in the presence of the olefin reactant. Uncomplexed rhodium catalyst may be used as finely distributed rhodium metal; water soluble rhodium salts, such as the chloride, the sulfate, or acetate; organically soluble compounds such as the 2-ethylhexanoate; or insoluble compounds such as the oxide. The rhodium concentration in the aqueous catalyst solution should be about 10 to about 2000 ppm relative to the solution.

The phosphine complexing agent is preferably used in an amount of 1–1000 mole, more preferably 2–300 mole, and most preferably 2–100 mole, of phosphine compound per g-atom of rhodium.

The pH of the catalyst solution can vary over wide ranges. Generally, it should be between 2 and 13. Preferably, the pH is 4–10. The synthesis gas ratio can also vary over wide ranges. Any proportion generally utilized in hydroformylations reaction is suitable. The most preferred volume ratio is carbon monoxide:hydrogen of about 1:1.

The remaining organic product phase, which is almost free of rhodium after the phase separation, is washed with water to remove the residual extracting or complexing agent, rhodium, and solubilizer, it can then be subjected to the usual distillation work-up if desired. The water used for washing can be recirculated. Since the Oxo raw product continually removes a small amount of water from the complexing agent solution, part of the wash water stream can be directed into the extraction stage to replace water losses and thereby prevent the complexing agent solution from becoming too concentrated. This amount of water is replaced in the washing stage or at any other convenient point by the addition of fresh water.

The aqueous phase, containing rhodium in high concentration, is fed into the reaction mixture, either directly or cleaned and concentrated, as a catalyst solution. It is also possible to separate the rhodium compounds which, but for the instant process, would be barely soluble or insoluble in water, e.g. in the form of rhodium-2-ethylhexanoate, and to re-use them as catalysts.

In the following examples various embodiments of the invention are described; the claimed process is not, however, limited to these embodiments.

EXAMPLES

In the Examples 1 to 8, raw isooctylaldehyde obtained by the hydroformylation of i-heptene cooled down to 20° to 25° C. and stored for several hours is used as the mixture from which rhodium is to be extracted. Examples 1, 3, 5 and 7 (the art) refer to rhodium extraction without the addition of a solubilizer; in Examples 2, 4, 6 and 8 (the invention) a solubilizer is used. In Examples 9 to 12, the separation of rhodium from various hydroformylation products is described. No solubilizer is used in Examples 9 and 11, while one is used in Examples 10 and 12.

The abbreviation TPPTS stands for triphenylphosphine trisulfonate. All concentrations are given in % by weight.

EXMAPLE 1 (COMPARISON)

In a flask fitted with a stirrer, 200 g of raw isooctylaldehyde containing
34.9% $C_7$ hydrocarbons (mainly heptene), 62.7% isooctylaldehyde,
2.2% isooctylalcohol,
0.2% higher boiling substances, and
3.9 ppm rhodium are mixed with 20 g of a 0.1% aqueous sodium TPPTS solution. The molar ratio of phosphorus to rhodium is 5:1. The two phases are intensively stirred for 5 minutes at 50° C. After completion of the stirring, the two phases separate within 12 seconds, without an emulsion being formed. The organic Oxo raw product still contains 1.1 ppm rhodium, corresponding to a rhodium separation of 72%.

EXAMPLE 2

Example 1 is repeated except that 0.1 g of cetyltrimethylammonium methosulfate is added to the aqueous TPPTS solution and the mixture stirred for 1 minute. The organic Oxo raw product phase only contains 0.6 ppm rhodium corresponding to a rhodium separation of 85%.

EXAMPLE 3 (COMPARISON)

Example 1 is repeated but a 0.4% sodium-TPPTS solution is used. The molar ratio of phosphorus to rhodium is 20:1. 1 ppm rhodium is left in the organic phase corresponding to a rhodium separation of 74%.

EXAMPLE 4

The same procedure used in Example 3 is carried out except that 0.1 g dodecyltrimethylammonium sulfate is added to the aqueous TPPTS solution and the mixture stirred for 1 minute. 0.6 ppm rhodium are left in the organic phase corresponding to a rhodium separation of 85%.

EXAMPLE 5 (COMPARISON)

Example 3 is repeated but the mixture is stirred at a temperature of 80° C. instead of 50° C. The two phases separate in 9 seconds. 1 ppm rhodium is left in the raw product corresponding to a rhodium separation of 74%.

EXAMPLE 6

The same procedure as in Example 5 is carried out except 0.1 g pyridinium sulfate is also added and the stirring time is 1 minute. Phase separation takes place in 9 seconds. 0.5 ppm rhodium is left in the raw product corresponding to a rhodium separation of 87%.

EXAMPLE 7 (COMPARISON)

In a round-bottom flask with an outlet at the bottom, a gas inlet capillary, and a stirrer, 1000 g of isooctyl aldehyde with the same composition as in Example 1 is repeatedly extracted, each time with 100 g of a 20% sodium TPPTS solution. Synthesis gas ($CO/H_2 = 1:1$) is fed through the inlet capillary to saturate the mixture with CO and hydrogen and the mixture is then intensively stirred at 80° C. and left to stand for a further 30 seconds. The aqueous phase is then drained through the bottom outlet and the organic phase treated again with the next 100 g of a 20% sodium TPPTS solution. The extraction process is carried out a total of four times. On completion, there is only 0.6 ppm rhodium left in the organic phase, corresponding to a rhodium separation of 85%.

EXAMPLE 8

Except that the extraction steps are carried out with a TPPTS solution which also contains 2 % benzyltrimethylammonium sulfate and the mixture is only stirred for 20 seconds, the procedure in Example 7 is repeated. After completion of the extraction steps only 0.3 ppm rhodium are left in the organic phase corresponding to a rhodium separation of 92%.

EXAMPLE 9 (COMPARISON)

In an apparatus used in Example 7, 1000 g of raw propionaldehyde containing
96.3% propionaldehyde,
0.2% n-propanol,
1.4% ethylene+ethane,
2.1% higher boiling substances, and
9.6 ppm rhodium are treated in 5 extraction steps, each time with 100 g of 20% sodium TPPTS solution at 86° C. The rhodium content of the organic phase is 1 ppm after the first extraction (corresponding to a rhodium separation of 66%) and 0.6 ppm after the fifth extraction (corresponding to a rhodium separation of 94%).

EXAMPLE 10

The same procedure used in Example 9 is carried out except that 2% cetyltrimethylammonium acetate is added to the aqueous TPPTS solution. The rhodium content of the organic phase after the first extraction is 0.6 ppm (corresponding to a rhodium separation of 94%) and 0.2 ppm after the fifth extraction (corresponding to a rhodium separation of 98%).

Improved results are also obtained with continuous operation.

EXAMPLE 11 (COMPARISON)

450 g of a residue from the hydroformylation of a $C_{20}$–$C_{40}$-$\alpha$-olefin mixture with a rhodium content of 17 ppm are extracted with 50 g of a 20% TPPTS solution in an autoclave at 100° C. After cooling and phase separation, the rhodium content of the non-distillable organic phase is 10 ppm, corresponding to a rhodium extraction of 41%.

EXAMPLE 12

Example 11 is repeated except that the aqueous TPPTS solution also contains 2.5% tetradecyltrimethylammonium lactate (based on the solution). The rhodium content of the organic phase after extraction is 0.2 ppm, corresponding to a rhodium recovery of 99%.

The example show that rhodium is extracted more rapidly and thoroughly when a solubilizer is added. Example 12 also demonstrates the rhodium catalyst can be removed from the non-distillable Oxo raw products under mild conditions.

In the remaining Examples, the following terms are utilized to characterize system efficiency.

n/i ratio of n-aldehyde to i-aldehyde $$\text{activity} = \frac{\text{mole aldehyde}}{\text{g-atom } Rh \times \text{min}}$$

$$\text{productivity} = \frac{\text{g aldehyde}}{\text{cm}^3 \text{ catalyst solution} \times \text{hours}}$$

$\phi$ is the average value of the repetitive trials reported in a particular Table Example 13 is a comparative example which is carried out without the addition of solubilizer.

EXAMPLE 13 (COMPARATIVE EXAMPLE)

a) Advance preparation of the catalyst 345 ml of an aqueous solution of trisodium-tri(m-sulfophenyl)-phosphine, with a content of 20.4% salt, and 400 ppm Rh, as rhodium acetate, are placed in a 1 litre autoclave with a support for a dip pipe. Synthesis gas ($CO/H_2$ volume ratio=1:1) is compressed to a pressure of 25 bar ($2.5 \times 10^3$ kPa). Then the reaction solution is treated for 3 hours with stirring at 125° C. with synthesis gas, during which time the active catalyst is formed. After the mixture has been cooled to about 30° C., stirring is stopped. After a settling period of 15 minutes the excess solution (~10 g) is forced out through the support and analysed. The rest of the solution remains in the autoclave.

b) Hydroformylation 170 g n-hexene-1 are pumped into the solution prepared according to a) and the mixture is stirred. At a constant pressure of 25 bar ($2.5 \times 10^3$ kPa) the mixture is heated to 125° C. and kept at this temperature for 3 hours. Afterwards, the mixture is cooled to 30° C. and left to settle. The upper organic phase is forced out through the support; it is weighed (see Table 1) and subjected to gas chromatographic analysis.

Step b) is repeated three times in total, basically the same results being achieved in each case. The activity and productivity figures listed in Table 1 refer to the amounts of organic and aqueous phase present in the autoclave. The specific weight of the aqueous phase is 1.1304.

TABLE 1

| Number of hydroformylations | 1 | 2 | 3 | 4 | φ |
|---|---|---|---|---|---|
| conversion (% acc. to GC) | 22 | 18 | 18 | 16 | 18 |
| n/i ratio | 98/2 | 98/2 | 98/2 | 98/2 | 98/2 |
| organic phase (g) | 153 | 167 | 172 | 175 | 167 |
| aqueous phase in the reactor (g) | 346 | 344 | 343 | 342 | 344 |
| activity $\frac{\text{mol } C_7 \text{ aldehydes}}{\text{g atom Rh} \times \text{min}}$ | 1.22 | 1.09 | 1.13 | 1.02 | 1.11 |
| productivity $\frac{\text{g } C_7 \text{ aldehydes}}{\text{cm}^3 \text{ cat. sol.} \times \text{h}}$ | 0.037 | 0.033 | 0.034 | 0.031 | 0.033 |

EXAMPLE 14

Example 13 is repeated except that 9.75 g (2,5 Gew.%) tetradecyltrimethylammonium methosulfate are added to the aqueous catalyst solution according to the invention. The specific weight of the catalyst solution is 1.171.

The test results are compiled in Table 2.

TABLE 2

| | 1 | 2 | 3 | 4 | 5 | φ |
|---|---|---|---|---|---|---|
| conversion (% acc. to GC) | 41 | 47 | 48 | 35 | 42 | 43 |
| n/i ratio | 95/5 | 96/4 | 96/4 | 96/4 | 96/4 | 96/4 |
| organic phase (g) | 168 | 175 | 185 | 220 | 176 | 185 |
| aqueous phase in the reactor (g) | 374 | 352 | 341 | 336 | 306 | 342 |
| activity $\frac{\text{mol } C_7 \text{ aldehydes}}{\text{g atom Rh} \times \text{min}}$ | 2.31 | 2.93 | 3.23 | 2.87 | 3.02 | 2.87 |
| productivity $\frac{\text{g } C_7 \text{ aldehydes}}{\text{cm}^3 \text{ cat. sol.} \times \text{h}}$ | 0.072 | 0.091 | 0.102 | 0.089 | 0.094 | 0.090 |

Example 14 shows that activity and productivity are considerably improved—from about 2 times to about 3 times—by the addition of a solubilizer, without adversely affecting the selectivity to any appreciable extent.

In order to determine the phosphorus and rhodium discharge, the organic products of Example 14 are mixed, concentrated and analysed. 0.3 ppm rhodium and 4 ppm phosphorus are contained in the organic product.

In Examples 15 to 21, the effect of the different solubilizers is clearly shown. The results of five hydroformylations with the same catalyst solution are summerized in an average value shown in Table 3. The test conditions are the same as in Examples 13 and 14.

TABLE 3

| Example/ No. of additive (see below) | 13 | 15 | 16 | 17 | 18 | 19 | 20 | 21 |
|---|---|---|---|---|---|---|---|---|
| amount (%) concentration (%) | — | 1 | 1 | 1 | 2.5 | 2.5 | 2.5 | 2.5 |
| conversion (% to GC) | 18 | 23 | 25 | 27 | 30 | 30 | 35 | 33 |
| activity $\frac{\text{mol } C_7 \text{ aldehyde}}{\text{g atom Rh} \times \text{min}}$ | 1.07 | 1.43 | 1.58 | 1.74 | 1.88 | 2.28 | 2.41 | 2.36 |
| productivity $\frac{\text{g } C_7 \text{ aldehyde}}{\text{cm}^3 \text{ cat. sol.} \times \text{h}}$ | 0.032 | 0.045 | 0.049 | 0.054 | 0.056 | 0.069 | 0.072 | 0.071 |

15 olyl alcohol (HD-Ocenol 150/170 manufacturer: Henkel KG)
16 lauryltrimethylammonium chloride
17 laurylpyridinium chloride
18 benzyltrimethylammonium sulfate
19 deodecyl-trimethylammonium methosulfonate
20 benzyltrimethylammonium lactate
21 diemthylethylhexadecylammonium benzene sulfate In the following examples, the concentration of the water-soluble trisulfonated phosphine is reduced so that the content of tri(m-sulfonphenyl) phosphine sodium salt is 12.2% by weight. Otherwise the same procedure as in Examples 13 to 14 is adopted. Again the average of five hydroformylations with the same catalyst solution is taken. The results are compiled in Table 4.

TABLE 4

| Example/No. of additive | 22 | 23 | 24 a) | 25 | 26 | 27 | 28 | 29 |
|---|---|---|---|---|---|---|---|---|
| concentration (%) | without | 5 | 2.5 | 0.5 | 2.5 | 2.5 | 2.5 | 2.5 |
| conversion (% acc. to GC) | 36 | 43 | 86 | 43 | 43.5 | 39 | 42 | 50 |
| activity $\frac{\text{mol } C_7 \text{ aldehyde}}{\text{g atom Rh} \times \text{min}}$ | 1.94 | 3.40 | 6.1 | 2.7 | 2.8 | 2.47 | 3.3 | 3.8 |
| productivity $\frac{\text{g } C_7 \text{ aldehyde}}{\text{cm}^3 \text{ cat. sol.} \times \text{h}}$ | 0.065 | 0.098 | 0.200 | 0.087 | 0.088 | 0.072 | 0.097 | 0.112 | a) φ 30 individual tests
23 polyglycol 200 (manufacturer: Hoechst AG)
24 trimethyl-hexadecylammonium bromide
25 trimethyl-hexadecylammonium bromide
26 triethylene glycol
27 Na salts of oleic acid
28 sulfolane
29 tributylhexadecylammonium lactate Comparison of Tables 3 and 4 shows the influence of the rhodium/phosphorus ratio on the extent of conversion in the hydroformylation process. In Table 4, the minimum activity, without solubilizer, is seen to be about 2. This is observed with a Rh/P ratio of about 1:50 and is about twice as high as that observed in Table 3 where the Rh/P ratio is 1:100. Surprisingly, the increase in conversion achieved as the Rh/P ratio drops is even more pronounced when the solubilizers of the invention are also present.

In order to determine the phosphorus and rhodium discharge the organic products of Example 24 are mixed, concentrated and analysed. 0.41 ppm rhodium and 6.63 ppm phosphorus are contained in the organic product.

What we claim is:

1. A process for the recovery of umcomplexed rhodium at a concentration of 3.9 to 17 ppm in an organic phase hydroformylation reaction product comprising extracting the organic phase reaction product with an aqueous solution of a sulfonate and/or carboxylate of organic phosphines of a formula

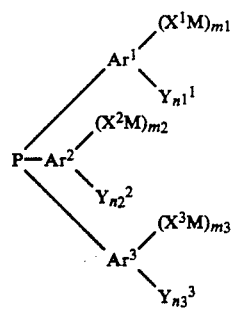

wherein $Ar^1$, $Ar^2$ and $Ar^3$ are individually selected form the group consisting of phenyl and naphthyl, $Y^1$, $Y^2$, and $Y^3$ are individually selected from the group consisting of alkyl and alkoxy of 1 to 4 carbon atoms, halogen, hydroxy, cyano, nitro and

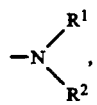

$R^1$ and $R^2$ are individually selected from the group consisting of carboxylate (COO—) and sulfonate (—SO$_3$—), $m_1$, $m_2$ and $m_3$ are individually an integer from 0 to 3 with the sum of $m_1$, $m_2$ and $m_3$ being at least one, $n_1$, $n_2$ and $n_3$ are individually integers form 0 to 5, M is selected from the group consisting of alkali-metal, alkaline earth metal, zinc, ammonium and quaternary ammonium ions of the formula $N(R_3R_4R_5R_6)^3$, $R_3$, $R_4$, $R_5$ and $R_6$ are individually alkyl of 1 to 4 carbon atoms in an amount of 2 to 300 moles of said phosphine per mole of rhodium and a solubilizer in an amount of 0.1 to 2.5% by weight based on the aqueous solution to recover more than 95% of the rhodium contained in the organic reaction product.

2. The process of claim 1 wherein said solubilizer is selected from the group consisting of phase transfer agents, surface active agents, amphiphilic reagents and tensiles.

3. The process of claim 1 wherein said solubilizer is selected from the group consisting of salts of carboxylic acids having 8-20 carbon atoms, alkyl sulfonates, alkyl aryl sulfonates, amines, quaternary ammonium compound salts, ethylene oxide adducts, sulfolane and dimethylsulfoxide.

4. The process of claim 3 wherein said carboxylic acids are saturated and have 12-18 carbon atoms; said alkyl aryl sulfonate is selected from alkyl benzene sulfonate and alkyl naphthalene sulfonate; said amines are selected from octadecyldiethylamine, octadecylethanolamine, laurylglycolamine, 2-heptadecylimidazoline hydrochloride, and hydrolysis-stable amine ethers; and said ethylene oxide adducts are selected from alkylpolyethylene glycol, alkylphenylpolyethyleneglycols, and acylpolyethylene glycols.

5. The process of claim 4 wherein said hydrolysis-stable amine ether is octylphenoldiethylamine ethylglycol ether;

6. The process of claim 3 wherein said quaternary ammonium compounds are of Formula II

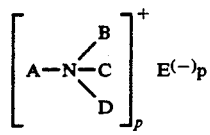

wherein A is a straight or branched alkyl, alkoxy, hydroxylalkyl, substituted or unsubstituted aryl having 6-25 carbon atoms, or $R^7CONHCH_2CH_2CH_2-$ wherein $R^7$ is a straight or branched alkyl having 5-11 carbon atoms;

B is a straight or branched alkyl having 1-25 carbon atoms, a substituted or unsubstituted aryl having 6-25 carbon atoms or ω-hydroxyalkyl having 1-4 carbon atoms;

C and D are each independently chosen from straight or branched alkyls or ω-hydroxyalkyl each having 1-4 carbon atoms, and C and D, together with the bridging N, may form a 5 or 6 membered heterocyclic ring; and E is selected from chloride, bromide, iodide, sulfate, tetrafluoroborate, acetate, methosulfate, benzene sulfate, alkylbenzene sulfate, sulfonate, toluene sulfonate, lactate, and citrate.

7. The process of claim 6 wherein A is selected from methyl, ethyl, propyl, stearyl, phenyl, benzyl, dodecyl, cetyl, myristyl, stearyl carbonyl, lauryl, heptanoic acid amide, propyl, and nonanoic acid amido propyl;

B is selected from methyl, ethyl, hydroxyethyl propyl, stearyl, phenyl, benzyl, dodecyl, cetyl, myrostyl, stearylcarbonyl, and lauryl., C and D are each independently selected from methyl, ethyl and hydroxyethyl; or at least two of B, C and D combine to form, with the bridging N, a pyrrole, pyridine or morpholine ring.

8. The process of claim 6 wherein said A is selected from straight or branched alkyl having 8-16 carbons and substituted or unsubstituted aryl having 10-14 carbon atoms.

9. The process of claim 1 wherein said hydroformylation reaction utilizes an olefin having at least 5 carbon atoms as a reactant.

10. The process of claim 1 wherein each of $Ar^1-Ar^3$ is phenyl, each of $X^1-X^3$ is sulfonate, and each of $m_1$, $m_2$ and $m_3$ is 0 or 1.

* * * * *